US009364293B2

(12) United States Patent
Shalgi et al.

(10) Patent No.: US 9,364,293 B2
(45) Date of Patent: Jun. 14, 2016

(54) REDUCED FIELD DISTORTION IN MEDICAL TOOLS

(75) Inventors: Avi Shalgi, Tel Aviv (IL); Yaacov Nitzan, Herzilya (IL); Meir Bar-Tal, Zichron Ya'acov (IL); Uri Yaron, Irvine, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 2393 days.

(21) Appl. No.: 11/414,449

(22) Filed: Apr. 28, 2006

(65) Prior Publication Data
US 2007/0255132 A1 Nov. 1, 2007

(51) Int. Cl.
*A61B 5/05* (2006.01)
*A61B 19/00* (2006.01)
*G01V 3/10* (2006.01)
*A61B 5/06* (2006.01)

(52) U.S. Cl.
CPC ............. *A61B 19/5244* (2013.01); *A61B 19/52* (2013.01); *G01V 3/104* (2013.01); *A61B 5/06* (2013.01); *A61B 2019/5251* (2013.01); *A61B 2019/5458* (2013.01)

(58) Field of Classification Search
USPC ........................ 606/61, 72; 600/407, 410, 409
See application file for complete search history.

(56) References Cited

U.S. PATENT DOCUMENTS

| | | |
|---|---|---|
| 3,350,962 A | 11/1967 | Muller et al. |
| 4,640,871 A | 2/1987 | Hayashi et al. |
| 5,391,199 A | 2/1995 | Ben-Haim |
| 5,443,489 A | 8/1995 | Ben-Haim |
| 5,555,251 A | 9/1996 | Kinanen |
| 5,738,632 A | 4/1998 | Karasawa |
| 5,767,669 A | 6/1998 | Hansen et al. |
| 5,913,820 A | 6/1999 | Bladen et al. |
| 6,147,480 A | 11/2000 | Osadchy et al. |
| 6,178,353 B1 | 1/2001 | Griffith et al. |
| 6,239,724 B1 | 5/2001 | Doron et al. |
| 6,332,089 B1 | 12/2001 | Acker et al. |
| 6,373,240 B1 | 4/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2003/0173964 A1 | 9/2003 | Yoshino et al. |
| 2004/0004477 A1 | 1/2004 | Nesteruk et al. |
| 2004/0034355 A1* | 2/2004 | Govari et al. ............. 606/72 |

(Continued)

FOREIGN PATENT DOCUMENTS

| | | |
|---|---|---|
| EP | 1849428 A2 | 10/2007 |
| GB | 719625 | 12/1954 |

(Continued)

OTHER PUBLICATIONS

Australia Exam Report for AU: 2007201850 Dated Jul. 25, 2011.

(Continued)

*Primary Examiner* — Joel F Brutus
(74) *Attorney, Agent, or Firm* — Louis J. Capezzuto

(57) ABSTRACT

A medical tool for operating in a working volume of a magnetic position tracking system includes a first plurality of layers including an electrically conductive material and a second plurality of layers including an electrically insulating material and interleaved with the first plurality. The layers are arranged to reduce eddy current distortion in a magnetic field generated by the magnetic position tracking system.

51 Claims, 3 Drawing Sheets

(56) References Cited

U.S. PATENT DOCUMENTS

| | | |
|---|---|---|
| 2004/0068178 A1 | 4/2004 | Govari |
| 2004/0102696 A1 | 5/2004 | Govari |
| 2004/0199069 A1 | 10/2004 | Connelly et al. |
| 2005/0049592 A1* | 3/2005 | Keith et al. ............... 606/61 |
| 2005/0096683 A1 | 5/2005 | Ellins et al. |
| 2005/0245821 A1 | 11/2005 | Govari et al. |
| 2005/0283067 A1 | 12/2005 | Sobe |

FOREIGN PATENT DOCUMENTS

| | | |
|---|---|---|
| JP | 59222758 | 12/1984 |
| JP | 61069103 | 4/1986 |
| JP | 1961069103 | 4/1986 |
| JP | 62501231 | 5/1987 |
| JP | 62175681 | 8/1987 |
| JP | 2004023411 | 4/1992 |
| JP | 2004126377 | 4/1992 |
| JP | 2005335137 | 12/1993 |
| JP | 6252586 | 9/1994 |
| JP | 197190710 | 7/1995 |
| JP | 197202468 | 8/1995 |
| JP | 09127220 | 11/1995 |
| JP | 7336086 | 12/1995 |
| JP | 07336086 | 12/1995 |
| JP | 09222006 | 2/1996 |
| JP | 10210692 | 1/1997 |
| JP | 9192114 | 7/1997 |
| JP | 11053463 | 2/1999 |
| JP | 2011153463 | 8/1999 |
| JP | 2001023838 | 1/2001 |
| JP | 2002063531 | 2/2002 |
| JP | 2002065631 | 3/2002 |
| JP | 2002365010 | 12/2002 |
| JP | 2003333813 | 11/2003 |
| JP | 2005278753 | 3/2004 |
| JP | 2004174244 | 6/2004 |
| JP | 2004536298 | 12/2004 |
| JP | 2005253965 | 3/2005 |
| JP | 2002236010 | 6/2005 |
| JP | 2005183652 | 7/2005 |
| JP | 2005198463 | 7/2005 |
| JP | 2005283067 | 10/2005 |
| JP | 2006049335 | 2/2006 |
| JP | 2003245243 | 3/2006 |
| JP | 2004199069 | 2/2007 |
| JP | 4023411 | 12/2007 |
| JP | 2008500441 | 1/2008 |
| JP | 2005096683 | 5/2008 |
| JP | 2008503248 | 7/2008 |
| JP | 5335137 | 11/2013 |
| WO | 94/04938 A1 | 3/1994 |
| WO | WO 96/05768 A1 | 2/1996 |
| WO | 03/001244 A1 | 1/2003 |
| WO | WO 2005/087125 | 9/2005 |
| WO | 2005/122884 A2 | 12/2005 |
| WO | WO 2006/023055 | 3/2006 |

OTHER PUBLICATIONS

Australia Exam Report for AU: 2007201850 Dated Jul. 2, 2014.
Australia Exam Report for AU: 2007201850 Dated Jun. 26, 2015.
Canada Office Action for CA2586416 Dated Dec. 12, 2013.
Canada Office Action for CA2586416 Dated Oct. 10, 2014.
China Office Action for CN200710100945.0 Dated Sep. 21, 2010.
China Office Action for CN200710100945.0 Dated Oct. 13, 2010.
China Office Action for CN200710100945.0 Dated Jun. 15, 2011.
China Office Action for CN200710100945.0 Dated Sep. 26, 2011.
China Office Action for CN200710100945.0 Dated Feb. 28, 2012.
EP Search Report for EP07251788 Dated Jun. 4, 2008.
EP Search Report for EP07251788 Dated Feb. 9, 2009.
Japan Office Action for JP2007118970 Dated Oct. 4, 2011.
Japan Office Action for JP2007118970 Dated Dec.18, 2012.
Japan Office Action for JP2007118970 Dated Nov. 12,2013.
Japan Office Action for JP2007118970 Dated Feb. 3, 2015.

\* cited by examiner

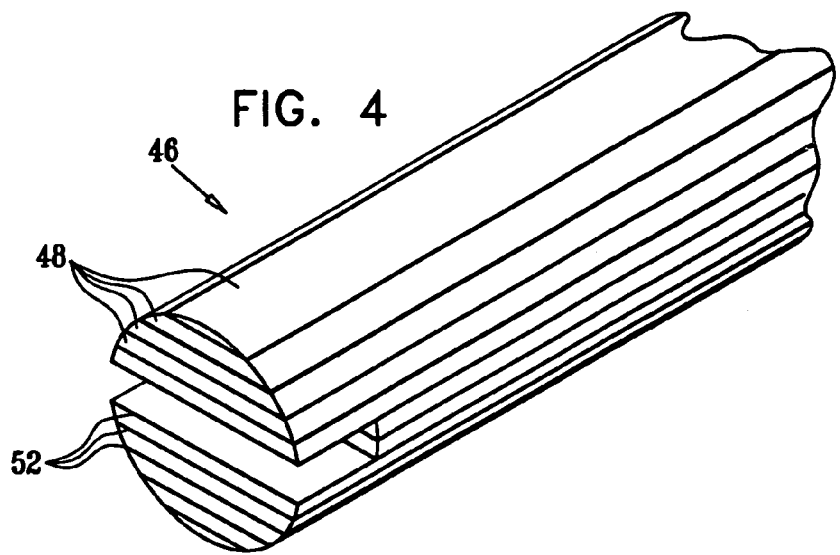
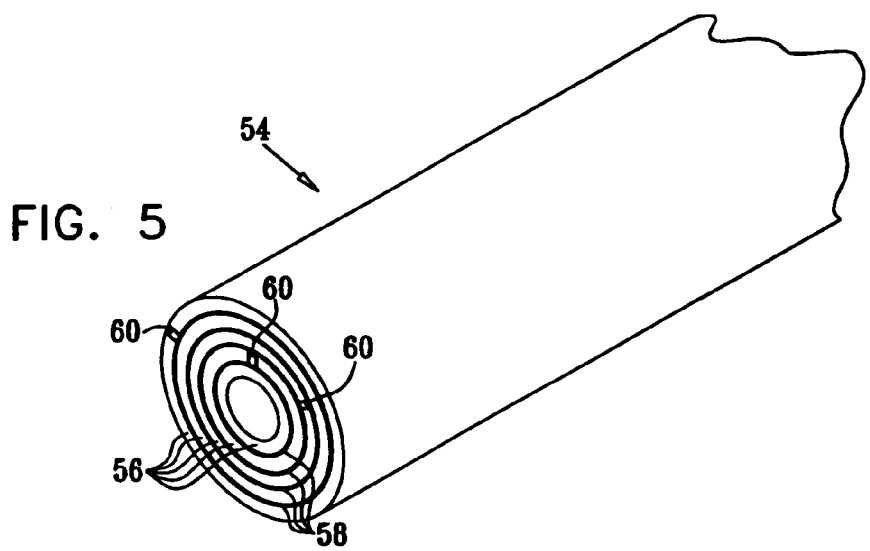
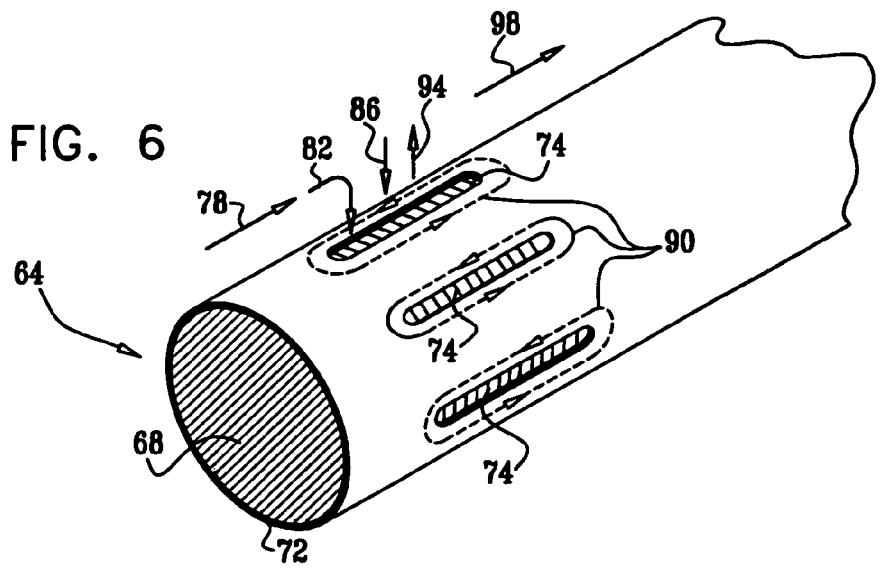

REDUCED FIELD DISTORTION IN MEDICAL TOOLS

FIELD OF THE INVENTION

The present invention relates generally to position tracking of medical intrabody devices and medical tools, and particularly to medical tools that cause reduced disturbance to position measurements in magnetic position tracking systems.

BACKGROUND OF THE INVENTION

Various methods and systems are known in the art for tracking the coordinates of objects involved in medical procedures. Some of these systems use magnetic field measurements. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations.

Additional methods and systems that relate to magnetic position tracking are also described, for example, in PCT Patent Publication WO 96/05768, U.S. Pat. Nos. 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. These publications describe methods and systems that track the position of intrabody objects such as cardiac catheters, orthopedic implants and medical tools used in different medical procedures.

It is well known in the art that the presence of medical and surgical tools comprising metallic, ferromagnetic and/or paramagnetic material within the magnetic field of a magnetic position tracking system often distorts the system measurements. In some cases the distortion is caused by eddy currents that are induced in such objects by the system's magnetic field. In other cases the interfering object distorts the system's magnetic field itself.

Various methods and systems have been described in the art for performing position tracking in the presence of such interference. For example, U.S. Pat. No. 6,147,480, whose disclosure is incorporated herein by reference, describes a method in which the signals induced in the tracked object are first detected in the absence of any articles that could cause parasitic signal components. Baseline phases of the signals are determined. When an article that generates parasitic magnetic fields is introduced into the vicinity of the tracked object, the phase shift of the induced signals due to the parasitic components is detected. The measured phase shifts are used to indicate that the position of the object may be inaccurate. The phase shifts are also used for analyzing the signals so as to remove at least a portion of the parasitic signal components.

Another application is described in U.S. Pat. No. 5,767,669, whose disclosure is incorporated herein by reference. The inventors describe a system for determining the position of remote sensors using pulsed magnetic fields. The fields are sensed by a remote sensor comprising a plurality of passive field sensing elements. Eddy current distortions are sensed separately and subtracted by the system. The system measures the effect of metallic objects present in the environment and dynamically adjusts the measured values accordingly. The sensed magnetic fields are used in order to calculate the position and orientation of the remote object.

Reduction of eddy currents induced in objects is sometimes implemented by constructing the objects from laminated layers of thin, metallic plates or from powdered-iron. For example, U.S. Pat. No. 6,178,353, whose disclosure is incorporated herein by reference, describes an implantable medical device that utilizes laminated, sectionalized or particle-based structures, so as to reduce the electrical energy absorbed by the implant device when in use. The inventors claim that this construction makes the implant device immune to being damaged by magnetic resonance imaging (MRI).

In some applications, the laminated plates are also slotted, in order to reduce eddy currents within the layers. For example, U.S. Pat. No. 5,555,251, whose disclosure is incorporated herein by reference, describes a method for constructing parts of a magnetic resonance medical imager using laminated layers cut from transformer sheet material. Each layer is electrically insulated from adjacent layers and surfaces by enamel or fixing glue. To reduce eddy currents in these layers, narrow, radially oriented slots are cut in the layers before lamination. The slots are oriented in the adjacent layers so as not to coincide. The inventors claim that this construction improves the conduction of the magnetic flux in the imaging volume.

In some applications, the material composition of medical tools is chosen so as to reduce the magnetic field distortion caused by the tool. For example, U.S. Pat. No. 6,258,071, whose disclosure is incorporated herein by reference, describes a medical needle made of non-metallic non-magnetic materials, such that medical interventional procedures requiring needle access to people, animals or isolated tissues can be performed in a Magnetic Resonance Imaging (MRI) scanner without significant artifact or image distortion. The dimensions of the needle are adaptable to the task required.

As another example, U.S. Pat. No. 5,738,632, whose disclosure is incorporated herein by reference, describes a device for use in combination with an MRI apparatus. The distal end portion of the device has a magnetic permeability of such a value that diagnosis and treatment are not influenced by magnetic resonance image distortions due to a disturbance to the uniformity of the static magnetic field generated by the MRI apparatus.

SUMMARY OF THE INVENTION

Magnetic position tracking systems often produce erroneous or inaccurate measurements when metallic, paramagnetic and/or ferromagnetic objects are present in the vicinity of the tracked object. Some of these errors are caused by eddy currents that are induced in the objects. Other errors are caused by distortion of the magnetic field lines by ferromagnetic materials.

Embodiments of the present invention provide improved methods for manufacturing and using medical tools that reduce the level of magnetic field distortion. As a result, tools manufactured and operated according to the disclosed methods produce lower distortion when subjected to a magnetic field, and thus reduce distortion-related errors in the position calculations of the magnetic position tracking system.

In some embodiments, eddy current distortion is reduced in a tool by applying electrical discontinuities, such as gaps or other openings to loop-shaped elements of the tool, so as to reduce induced eddy currents. In other embodiments, the medical tool comprises a laminated structure of electrically-conducting layers separated by electrically-insulating layers.

The interleaved structure limits the potential conductive surfaces over which eddy current loops can form.

In some embodiments, distortion related to ferromagnetic materials is reduced by applying to the ferromagnetic tool an electrically-conductive coating comprising a paramagnetic material. Optionally, a pattern of slots is introduced into the coating. The coating and/or slots are configured so that eddy current loops induced in the coating produce a parasitic field that cancels at least part of the field distortion caused by the ferromagnetic material.

The methods, systems and tools disclosed herein can be used either independently, in combination with one another, or in conjunction with any parasitic field compensation method, such as the methods described in U.S. Pat. Nos. 6,147,480 and 5,767,669 cited above.

There is therefore provided, in accordance with an embodiment of the present invention, a system for treatment of a body of a patient, including:

a magnetic position tracking system, including:

a first field transducer, which is arranged to generate a magnetic field;

a second field transducer, which is arranged to sense the magnetic field and generate a signal responsively to the sensed field, wherein one of the field transducers is coupled to an object for insertion into the body; and a control unit, which is arranged to process the signal so as to determine a position of the object; and a medical tool for use in the treatment of the body, the tool including a first plurality of layers including an electrically conductive material, interleaved with a second plurality of layers including an electrically insulating material, wherein the layers are arranged to reduce eddy current distortion in the magnetic field sensed by the second field transducer.

In an embodiment, the layers in the first and second pluralities respectively include first and second planar layers. In another embodiment, the tool has an axis, and the layers in the first and second pluralities respectively include first and second annular layers surrounding the axis. Additionally or alternatively, at least one of the layers in the first plurality has an electrical discontinuity introduced therein so as to reduce the eddy current distortion.

In yet another embodiment, the medical tool includes an orthopedic tool, and the object includes an orthopedic implant. In still another embodiment, the second plurality of layers includes at least one of an adhesive material applied between the first plurality of layers and an electrically insulating coating layer applied to the first plurality of layers.

In an embodiment, the tool includes a core including a ferromagnetic material and an outer coating layer on the core, the coating layer including a conductive material configured so as to produce eddy current distortion responsively to the magnetic field so as to cancel at least part of a distortion caused by the core in the magnetic field sensed by the second field transducer. In another embodiment, the tool includes an electrically conducting loop-shaped element having an electrical discontinuity introduced therein so as to reduce eddy current distortion caused by the loop-shaped element in the magnetic field sensed by the second field transducer.

In an embodiment, the system includes a third field transducer coupled to the medical tool, and the control unit is further arranged to determine a position of the medical tool using the third field transducer.

In another embodiment, the first field transducer includes a field generator external to the body, and the second field transducer includes a position sensor coupled to the object. Alternatively, the first field transducer includes a field generator coupled to the object, and the second field transducer includes a position sensor external to the body.

There is also provided, in accordance with an embodiment of the present invention, a system for treatment of a body of a patient, including:

a magnetic position tracking system, including:

a first field transducer, which is arranged to generate a magnetic field;

a second field transducer, which is arranged to sense the magnetic field and generate a signal responsively to the sensed field, wherein one of the field transducers is coupled to an object for insertion into the body; and a control unit, which is arranged to process the signal so as to determine a position of the object; and a medical tool for use in the treatment of the body, the tool including a core including a ferromagnetic material and an outer coating layer on the core, the coating layer including a conductive material configured to produce eddy current distortion responsively to the magnetic field so as to cancel at least part of a distortion caused by the core in the magnetic field sensed by the second field transducer.

In an embodiment, the outer coating layer includes copper. Additionally or alternatively, the outer coating layer has a pattern of slots formed therein so as to control a formation of the eddy current distortion caused by the coating layer.

There is further provided, in accordance with an embodiment of the present invention, a system for treatment of a body of a patient, including:

a magnetic position tracking system, including:

a first field transducer, which is arranged to generate a magnetic field;

a second field transducer, which is arranged to sense the magnetic field and generate a signal responsively to the sensed field, wherein one of the field transducers is coupled to an object for insertion into the body; and a control unit, which is arranged to process the signal so as to determine a position of the object; and a medical tool for use in the treatment of the body, the tool including an electrically conducting loop-shaped element having an electrical discontinuity introduced therein so as to reduce eddy current distortion caused by the loop-shaped element in the magnetic field sensed by the second field transducer.

In an embodiment, the loop-shaped element includes at least one of a handle and a loop-shaped cross-section of the tool.

There is additionally provided, in accordance with an embodiment of the present invention, a medical tool for operating in a working volume of a magnetic position tracking system, the tool including:

a first plurality of layers including an electrically conductive material; and a second plurality of layers including an electrically insulating material and interleaved with the first plurality, wherein the layers are arranged to reduce eddy current distortion in a magnetic field generated by the magnetic position tracking system.

There is also provided, in accordance with an embodiment of the present invention, a medical tool for operating in a working volume of a magnetic position tracking system, the tool including:

a core including a ferromagnetic material; and an outer coating layer on the core, the coating layer including a conductive material configured to produce eddy current distortion responsively to the magnetic field so as to cancel at least part of a distortion caused by the core in a magnetic field generated by the magnetic position tracking system.

There is further provided, in accordance with an embodiment of the present invention, a medical tool for operating in a working volume of a magnetic position tracking system, the tool including an electrically conducting loop-shaped element having an electrical discontinuity introduced therein, so as to reduce eddy current distortion caused by the loop-shaped element in a magnetic field generated by the magnetic position tracking system.

There is additionally provided, in accordance with an embodiment of the present invention, a method for treatment of a body of a patient, including:

generating a magnetic field using a first field transducer;

sensing the magnetic field using a second field transducer, wherein one of the field transducers is coupled to an object in the body, so as to determine a position of the object; and treating the body using a medical tool, which includes a first plurality of layers including an electrically conductive material, interleaved with a second plurality of layers including an electrically insulating material, wherein the layers are arranged to reduce eddy current distortion in the magnetic field sensed by the second field transducer.

There is also provided, in accordance with an embodiment of the present invention, a method for treatment of a body of a patient, including:

generating a magnetic field using a first field transducer;

sensing the magnetic field using a second field transducer, wherein one of the field transducers is coupled to an object in the body, so as to determine a position of the object; and treating the body using a medical tool, which includes a core including a ferromagnetic material and an outer coating layer on the core, the coating layer including a conductive material configured to produce eddy current distortion responsively to the magnetic field so as to cancel at least some of a distortion caused by the core in the magnetic field sensed by the second field transducer.

There is further provided, in accordance with an embodiment of the present invention, a method for treatment of a body of a patient, including:

generating a magnetic field using a first field transducer;

sensing the magnetic field using a second field transducer, wherein one of the field transducers is coupled to an object in the body, so as to determine a position of the object; and treating the body using a medical tool, which includes an electrically conducting loop-shaped element having an electrical discontinuity introduced therein, so as to reduce eddy current distortion caused by the loop-shaped element in the magnetic field sensed by the second field transducer.

There is also provided, in accordance with an embodiment of the present invention, a method for manufacturing a medical tool for operating in a working volume of a magnetic position tracking system, the method including:

forming a first plurality of layers including an electrically conductive material; and interleaving the first plurality with a second plurality of layers including an electrically insulating material, wherein the layers are arranged to reduce eddy current distortion in a magnetic field generated by the magnetic position tracking system.

There is additionally provided, in accordance with an embodiment of the present invention, a method for manufacturing a medical tool for operating in a working volume of a magnetic position tracking system, the method including:

forming a core of the tool, the core including a ferromagnetic material; and coating the core with an outer coating layer, the coating layer including a conductive material configured to produce eddy current distortion so as to cancel at least part of a distortion caused by the core when subjecting the tool to a magnetic field in the working volume.

There is further provided, in accordance with an embodiment of the present invention, a method for manufacturing a medical tool for operating in a working volume of a magnetic position tracking system, the method including:

identifying an electrically conducting loop-shaped element in the tool; and introducing an electrical discontinuity into the loop-shaped element, so as to reduce eddy current distortion caused by the loop-shaped element in a magnetic field generated by the magnetic position tracking system.

The present invention will be more fully understood from the following detailed description of the embodiments thereof, taken together with the drawings in which:

BRIEF DESCRIPTION OF THE DRAWINGS

FIGS. 2-6 are schematic, pictorial illustrations of medical tools, in accordance with embodiments of the present invention.

DETAILED DESCRIPTION OF EMBODIMENTS

System Description

Figure 1:
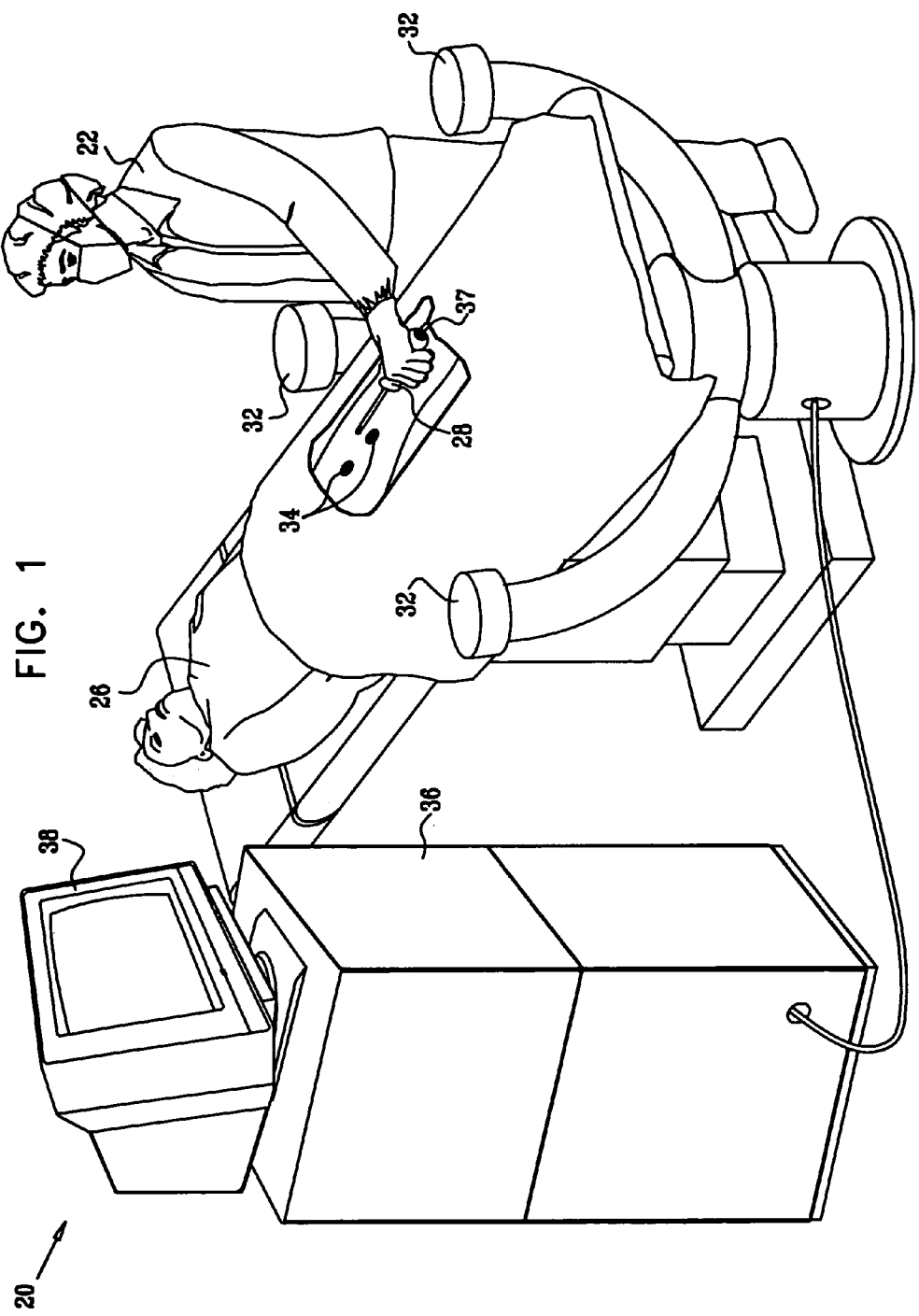
FIG. 1 is a schematic, pictorial illustration of a magnetic tracking system used in surgery, in accordance with an embodiment of the present invention.

FIG. 1 is a schematic, pictorial illustration of a magnetic tracking system 20 used in surgery, in accordance with an embodiment of the present invention. A surgeon 22 performs a medical procedure on a patient 26 using a medical tool 28. System 20 comprises field generators 32, which generate magnetic fields throughout a predetermined working volume that comprises the surgical site. The fields are generated in response to drive signals generated by a console 36. The magnetic fields are sensed by miniature, wireless transducers 34 introduced into the patient's body. In the example shown in FIG. 1, the transducers are fitted into orthopedic implants that are implanted into the patient's leg.

Each transducer comprises a position sensor that is designed to sense the magnetic field in its vicinity. The magnetic fields generated by field generators 32 induce currents in the position sensors of transducers 34. In response to the induced currents, signal processing and transmitter circuits in each transducer generate and transmit position signals that are indicative of the location and orientation coordinates of the transducer.

The position signals are typically received by a wireless control unit, which is coupled to a computer, both located in console 36. The computer processes the received position signals and calculates the location and orientation coordinates of transducers 34. The results are typically presented to the surgeon on a display 38.

The tracking system guides the surgeon in performing the procedure by measuring and presenting the positions of transducers 34. In some applications, a transducer 37 similar to transducers 34 is also fitted into tool 28. In such application, the tracking system measures and presents the position of the tool with respect to the intrabody transducers.

In an alternative embodiment, field generators are fitted into orthopedic implants or other intrabody objects, and transducers comprising position sensors are located externally to the patient body. In these embodiments, the intrabody field generators produce magnetic fields that are sensed and converted into position signals by the external position sensors. Console 36 calculates and displays the position of the intrabody field generators based on the position signals produced by the external position sensors. In general, both the field generators and position sensors are referred to as field transducers.

The configuration of system 20 shown in FIG. 1 was chosen for the sake of conceptual clarity. The methods and devices disclosed herein may be implemented in conjunction with any other suitable magnetic position tracking system, such as the systems described in U.S. Pat. Nos. 6,690,963, 6,618,612 and 6,332,089, and U.S. Patent Application Publications 2002/0065455 A1, and 2004/0068178 A1 cited above. In particular, a magnetic position tracking system for orthopedic applications is described in U.S. Provisional Patent Application No. 60/550,924, filed Mar. 5, 2004, now filed as U.S. patent application Ser. No. 11/062,258 filed on Feb. 18, 2005, whose disclosure is incorporated herein by reference. The principles of the present invention may similarly be implemented to reduce field distortion in magnetic tracking systems that are used for other applications, such as cardiovascular catheterization, endoscopy and other types of surgery.

Tool 28 may comprise any medical or surgical tool such as the orthopedic implant insertion tool described above, a scalpel, forceps, scissors or clamps. Additionally or alternatively, tool 28 may comprise any other object introduced into the working volume, such as an operating table or parts thereof, or other medical instrumentation units.

In many cases, medical and surgical tools are made of metal or comprise metallic parts. Additionally or alternatively, tools sometimes comprise parts made of ferromagnetic materials or materials that exhibit high magnetic permeability. For simplicity of explanation, in the context of the present patent application and in the claims, ferromagnetic, paramagnetic and/or metallic materials are collectively referred to herein as field-distorting materials. The term "field-distorting tool" is used to describe tools made of field-distorting material, as well as tools comprising parts made of such materials or otherwise having some field-distorting material content.

Reduction of Eddy Current Distortion

It is well known in the art that the presence of a field-distorting object, such as a metallic tool, inside a magnetic field often causes eddy currents to be induced in the tool. More accurately, eddy currents are induced in response to variations in the magnetic flux flowing through the metallic tool. Such variations occur, for example, when the tool is in motion or when the magnetic field changes. In practical scenarios relevant to magnetic tracking systems, eddy currents are typically induced in a metallic tool when the tracking system uses an alternating magnetic field (sometimes referred to as an "AC magnetic field," since it is generated in response to an Alternating-Current drive signal).

The eddy currents that flow in the tool typically take the form of current loops, flowing across metallic surfaces of the tool. These current loops generate secondary, or parasitic, magnetic fields. When a field-distorting tool is located inside the working volume, in the vicinity of transducer 34, the position sensor of the transducer senses a composite magnetic field. The composite field comprises a vector superposition of the primary magnetic field generated by field generators 32 and the parasitic magnetic field generated by the tool. Since the composite field is different from the original, primary field, the position signals transmitted by the transducer will typically be distorted. The distorted position signals will typically cause the computer to calculate an erroneous position of transducer 34.

Embodiments of the present invention provide improved methods for constructing tool 28, so as to reduce the level of eddy currents induced in the tool when it is subjected to the primary magnetic field. Using such a tool reduces position tracking errors in comparison to known tools.

Figure 2:
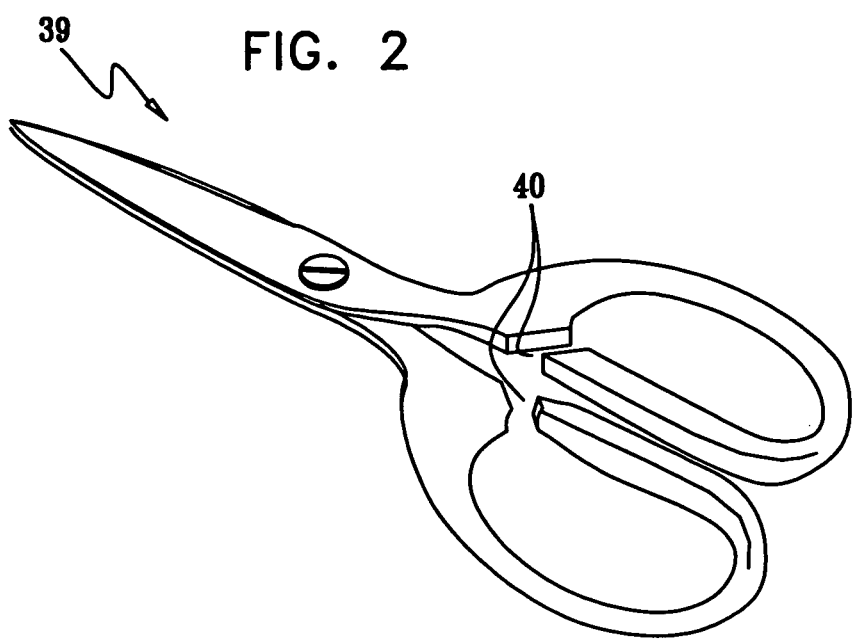

FIG. 2 is a schematic, pictorial illustration showing a tool 39, in accordance with an embodiment of the present invention. In the example of FIG. 2, tool 39 comprises a pair of scissors made of metallic material. As can be seen in the figure, the handles of scissors 39 have the general shape of a loop. Since eddy currents typically flow in paths having the shape of closed loops, loop-shaped electrically-conducting elements in the tool, such as the handles shown in FIG. 2, are particularly sensitive to eddy current induction. In some embodiments, electrical discontinuities, such as gaps 40 are introduced in the handles of the scissors, so as to disrupt closed loop-shaped electrically-conducting paths and reduce eddy currents.

Scissors 39 shown in FIG. 2 are chosen as an exemplary embodiment. Other medical tools such as surgical forceps, as well as other objects, comprise electrically-conducting loop-shaped elements that may form closed conducting paths for eddy currents. Introducing electrical discontinuities that break the closed conducting path significantly reduces the eddy currents induced in such objects, thus reducing the field distortion caused by the object. In some embodiments, the discontinuities may comprise air gaps, gaps filled with electrically-insulating material, or any other suitable type of electrical discontinuity.

Figure 3:
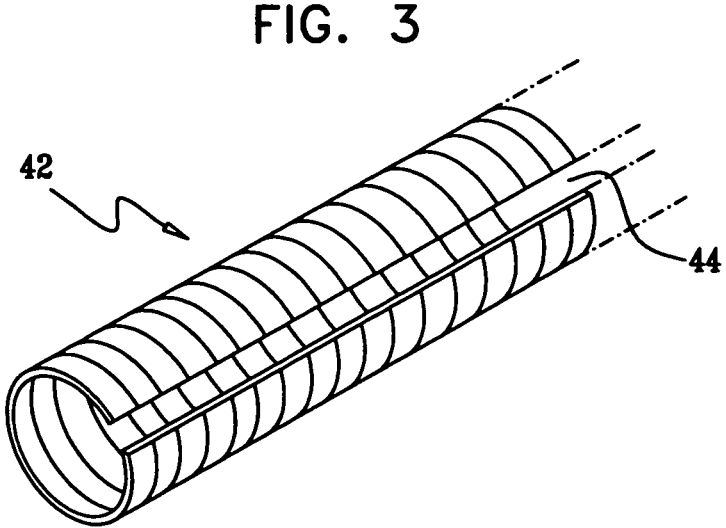

FIG. 3 is a schematic, pictorial illustration showing a part of a tool 42, in accordance with another embodiment of the present invention. In the example of FIG. 3 tool 42 comprises a tool having a cylindrical shaft, such as a screwdriver. The part shown in the figure is the shaft of the tool. The shaft can be seen to have a hollow, cylindrical shape. The cross-section of the shaft has a circular shape. Objects having a closed loop cross-section are another example of a closed electrically-conducting loop-shaped element that may cause strong eddy currents.

In order to minimize the eddy currents induced in tool 42, the shaft is constructed so as to leave an open air gap 44 and avoid fully-closed cylinder geometry. The loop-shaped element is disrupted by gap 44. As a result, the parasitic magnetic field generated by tool 42 is significantly lower than the field generated by a tool having an equivalent shape and comprising a fully-closed electrically-conducting cross-section.

In alternative embodiments, other types of electrical discontinuities may be used instead of air gap 44, such as gaps filled with electrically-insulating material. Although the example of FIG. 3 refers to a cylindrical shaft of a tool, the construction method described above can be used to construct any other suitable tool or tool part, such as, for example, screws, drills, tool handles, manipulators and retractors.

FIG. 4 is a schematic, pictorial illustration showing a part of a tool 46, in accordance with yet another embodiment of the present invention. In the present example, tool 46 comprises an orthopedic insertion tool, such as tool 28 described in FIG. 1 above. The part shown in the figure is the shaft of the tool. Tool 46 comprises a plurality of laminated layers 48. Each layer 48 typically comprises a thin, metallic layer that is given the desired shape. Adjacent layers 48 are electrically separated by electrically-insulating layers 52. In the example of FIG. 4, the layers are planar. Alternative layer configurations are described below.

In one embodiment, layers 52 comprise electrically-insulating adhesive material that bonds layers 48 together, while providing electrical insulation between layers 48. Alternatively, layers 40 may be coated with a suitable electrically-insulating coating, such as enamel, before bonding them together. Further alternatively, any other suitable manufacturing process may be used to produce an interleaved structure of electrically-conductive layers 48 and electrically-insulating layers 52. Additionally or alternatively, an interleaved stack of layers 48 and 52 can be manufactured having any convenient dimensions. The stack is then machined or otherwise processed to provide the desired three-dimensional shape of tool 46.

FIG. 5 is a schematic, pictorial illustration showing a part of a tool 54, in accordance with an alternative embodiment of the present invention. The figure shows an alternative method of constructing an interleaved structure of electrically-conducting and electrically-insulating layers used for reducing eddy current distortion. Tool 54 comprises a cylindrical tool, such as a screwdriver shaft or an orthopedic implant insertion tool. Unlike the embodiment of FIG. 4 above in which the layers are formed in a planar configuration, in the present example, electrically-conducting layers 56 and electrically-insulating layers 58 are arranged in a cylindrical, concentric configuration.

The cylindrical layer configuration shown in FIG. 5 is an exemplary configuration chosen to demonstrate a construction method in which annular-shaped electrically-conducting and electrically-insulating layers are interleaved with one another, surrounding an axis of the tool or tool part. The structure can have any desired cross section, such as a circular or oval cross-section, or any other arbitrary shape derived from the geometry of the tool.

In some embodiments, electrical discontinuities are introduced into electrically-conducting layers 56 in order to break eddy current loops within the layers. For example, FIG. 5 shows longitudal gaps 60 in layers 56. Gaps 60 are similar in structure and in function to air gaps 44 shown in FIG. 3 above. Similar discontinuities can also be introduced into the laminated structure of FIG. 4 above.

The construction methods described in FIGS. 4 and 5 above significantly reduce the level of eddy currents induced in tools 46 and 54. Since eddy currents can only flow into electrically-conductive surfaces, the electrical insulation provided by the electrically-insulating layers eliminates many of the potential surfaces and current loops over which eddy currents can flow. The parasitic magnetic field generated by the tool is thus significantly lower than the field generated by a tool having an equivalent shape and comprising a single electrically-conductive body.

In order to provide effective eddy current reduction, the thickness of the electrically-conductive layers is determined as a function of the electrical conductivity of the material used and of the frequency of the primary AC magnetic field. Typically, a thickness on the order of 1 mm is chosen, although other thicknesses can also be used.

Although the construction methods are demonstrated in FIGS. 4 and 5 above using the shaft of an insertion tool, these methods can be used to construct any other suitable tool or object in order to reduce the eddy current distortion it may cause.

In some embodiments, the eddy current distortion of tools constructed using the methods described in FIGS. 2-5 above can be further reduced by selecting the material composition of the tool to have lower electrical conductivity. For example, constructing tools using stainless steel series 316 or similar material significantly reduces the eddy current induced in the tools.

Reduction of Distortion in Ferromagnetic Tools

Another type of field distortion is associated with tools comprising ferromagnetic materials, such as iron. When a ferromagnetic field-distorting tool is introduced into the magnetic field of a magnetic position tracking system, the ferromagnetic material attracts and distorts the magnetic field lines in its vicinity. The field distortion often causes the position sensors in transducers 34 to produce distorted position signals, which in turn introduce errors into the position tracking calculations of the system.

Embodiments of the present invention provide improved methods for constructing medical tools, so as to reduce the ferromagnetic material related distortion of the tool when it is subjected to the magnetic field of the position tracking system. Using such tools reduces position tracking errors in comparison to known tools.

FIG. 6 is a schematic, pictorial illustration showing a part of a tool 64, in accordance with another alternative embodiment of the present invention. In this example, the part shown has a cylindrical shape, such as a screwdriver shaft or the shaft of orthopedic insertion tool 46 shown in FIG. 4 above. The shaft of tool 64 comprises a core 68 made of solid ferromagnetic material.

In principle, the method described below reduces the distortion caused by the ferromagnetic material by intentionally introducing a certain amount of eddy current distortion, which cancels out at least part of the ferromagnetic distortion. Core 68 is coated with an electrically-conductive coating 72. In some embodiments, coating 72 comprises an electrically-conducting material having a shallow skin depth, such as copper. Longitudal slots 74 are formed in coating layer 72 in order to control the formation of eddy current loops.

Consider, for example, a scenario in which tool 64 is positioned in parallel to the primary magnetic field. An arrow 78 in FIG. 6 shows the direction of the primary field. Ferromagnetic core 68 distorts the primary field by attracting field lines towards the tool, as shown by an arrow 82. The distorted field described by arrow 82 can thus be represented as a sum of the original primary field (arrow 78) and a distortion component shown by an arrow 86, which points into the tool.

The distorted field induces eddy currents in coating layer 72. Slots 74 control the formation of the eddy currents and directs the current to flow in current loops 90 around the slots. Current loops 90 in turn produce parasitic magnetic fields that are perpendicular to the plane of the loops. An arrow 94 shows the direction of the parasitic field at a particular location on the tool surface. The parasitic field (arrow 94) has an opposite direction in comparison to the distortion component (arrow 86). Thus, the parasitic field produced by the slotted coating layer cancels out at least part of the ferromagnetic-related distortion component. Overall, the primary field in the vicinity of tool 64 is undistorted, as shown by an arrow 98.

The configuration shown in FIG. 6 is an exemplary configuration used for the sake of conceptual clarity. In alternative embodiments, any other suitable coating configuration can be used for introducing a measured amount of eddy current distortion, in order to cancel at least some magnetic field distortion caused by ferromagnetic materials. In the context of the present patent application and in the claims, the term "slot" is used to refer to an electrical discontinuity in coating 68 having any suitable shape or size used for directing or controlling the formation of eddy current loops.

The construction method described in FIG. 6 can be used for reducing the distortion caused by other types of ferromagnetic objects. For example, ferromagnetic parts of an operating table, on which the patient lies, can be coated with a suitable coating layer. As another example, springs that are usually made of ferromagnetic materials can also be coated and treated using this method.

Combined Construction Methods

In some embodiments, two or more of the construction methods described in FIGS. 2-6 above can be combined in the construction of a particular tool. In a typical design process, the geometry of the tool is analyzed, along with other requirements. A combination of construction methods that best fits the particular tool is selected and applied in the construction of the tool.

For example, surgical forceps may be constructed using a thin and strong paramagnetic material, such as series 316 stainless steel or titanium. Gaps may be introduced into the handles to break the closed, loop-shaped handles. As another example, an operating table may be constructed out of hollow metallic parts wherever feasible, to minimize the amount of field-distorting material content. Ferromagnetic parts of the table can be coated with a conductive coating layer. Slots or other discontinuities can be added to break eddy current loops.

In some embodiments, the construction methods described in FIGS. 2-6 above can also be used in combination with methods for sensing and canceling out the effects of eddy currents in magnetic positioning systems, such as the methods described in U.S. Pat. Nos. 6,147,480 and 5,767,669 cited above.

While the disclosed methods and devices mainly address the construction of medical instruments used within the magnetic field of a position tracking system, other applications can use the principles described herein. For example, parts of intrabody objects such as orthopedic implants, various invasive medical instruments, catheters, endoscopes, gastroscopes, bronchoscopes, biopsy tools and needles can be manufactured using the disclosed methods.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A system for treatment of a body of a patient, comprising:
    a magnetic position tracking system, comprising:
        a first field transducer, which is arranged to generate a magnetic field;
        a second field transducer, which is arranged to sense the magnetic field and generate a signal responsively to the sensed field,
        wherein the second field transducers is coupled to an implant for insertion into the body; and
        a control unit, which is arranged to process the signal so as to determine a position of the implant in the body; and
    a medical tool for use in the body, the tool comprising a first plurality of layers comprising an electrically conductive material, interleaved with a second plurality of layers comprising an electrically insulating material, wherein the layers are arranged to reduce eddy current distortion in the magnetic field sensed by the second field transducer coupled to the implant.

2. The system according to claim 1, wherein the layers in the first and second pluralities respectively comprise first and second planar layers.

3. The system according to claim 1, wherein the tool has an axis, and wherein the layers in the first and second pluralities respectively comprise first and second annular layers surrounding the axis.

4. The system according to claim 1, wherein at least one of the layers in the first plurality has an electrical discontinuity introduced therein so as to reduce the eddy current distortion.

5. The system according to claim 1, wherein the medical tool comprises an orthopedic tool, and wherein the implant comprises an orthopedic implant.

6. The system according to claim 1, wherein the second plurality of layers comprises at least one of an adhesive material applied between the first plurality of layers and an electrically insulating coating layer applied to the first plurality of layers.

7. The system according to claim 1, wherein the tool comprises a core comprising a ferromagnetic material and an outer coating layer on the core, the coating layer comprising a conductive material configured so as to produce eddy current distortion responsively to the magnetic field so as to cancel at least part of a distortion caused by the core in the magnetic field sensed by the second field transducer.

8. The system according to claim 1, wherein the tool comprises an electrically conducting loop-shaped element having an electrical discontinuity introduced therein so as to reduce eddy current distortion caused by the loop-shaped element in the magnetic field sensed by the second field transducer.

9. The system according to claim 1, and comprising a third field transducer coupled to the medical tool, wherein the control unit is further arranged to determine a position of the medical tool using the third field transducer.

10. The system according to claim 1, wherein the first field transducer comprises a field generator external to the body, and wherein the second field transducer comprises a position sensor coupled to the implant.

11. The system according to claim 1, wherein the first field transducer comprises a field generator coupled to the implant, and wherein the second field transducer comprises a position sensor external to the body.

12. A system for treatment of a body of a patient, comprising:
    a magnetic position tracking system, comprising:
        a first field transducer, which is arranged to generate a magnetic field;
        a second field transducer, which is arranged to sense the magnetic field and generate a signal responsively to the sensed field,
        wherein second the field transducers is coupled to an implant for insertion into the body; and
        a control unit, which is arranged to process the signal so as to determine a position of the implant in the body; and
    a medical tool for use in the body, the tool comprising a core comprising a ferromagnetic material and an outer coating layer on the core, the coating layer comprising a conductive material configured to produce eddy current distortion responsively to the magnetic field so as to cancel at least part of a distortion caused by the core in the magnetic field sensed by the second field transducer coupled to the implant.

13. The system according to claim 12, wherein the medical tool comprises an orthopedic tool, and wherein the implant comprises an orthopedic implant.

14. The system according to claim 12, wherein the outer coating layer comprises copper.

15. The system according to claim 12, wherein the outer coating layer has a pattern of slots formed therein so as to control a formation of the eddy current distortion caused by the coating layer.

16. The system according to claim 12, wherein the tool comprises an electrically conducting loop-shaped element having an electrical discontinuity introduced therein so as to reduce eddy current distortion caused by the loop-shaped element in the magnetic field sensed by the second field transducer.

17. A medical tool for operating in a working volume of a magnetic position tracking system, the tool comprising:
 a first plurality of layers comprising an electrically conductive material; and
 a second plurality of layers comprising an electrically insulating material and interleaved with the first plurality, wherein the layers are arranged to reduce eddy current distortion in a magnetic field generated by the magnetic position tracking system.

18. The tool according to claim 17, wherein the layers in the first and second pluralities respectively comprise first and second planar layers.

19. The tool according to claim 17, wherein the tool has an axis, and wherein the layers in the first and second pluralities respectively comprise first and second annular layers surrounding the axis.

20. The tool according to claim 17, wherein at least one of the layers in the first plurality has an electrical discontinuity introduced therein so as to reduce the eddy current distortion.

21. The tool according to claim 17, wherein the medical tool comprises an orthopedic tool for use with orthopedic implants.

22. The tool according to claim 17, wherein the second plurality of layers comprises at least one of an adhesive material applied between the first plurality of layers and an electrically insulating coating layer applied to the first plurality of layers.

23. The tool according to claim 17, wherein the tool further comprises a core comprising a ferromagnetic material and an outer coating layer on the core, the coating layer comprising a conductive material configured to produce eddy current distortion responsively to the magnetic field so as to cancel at least part of a distortion caused by the core in the magnetic field generated by the magnetic position tracking system.

24. The tool according to claim 17, wherein the tool further comprises an electrically conducting loop-shaped element having an electrical discontinuity introduced therein so as to reduce eddy current distortion caused by the loop-shaped element in the magnetic field generated by the magnetic position tracking system.

25. A medical tool for operating in a working volume of a magnetic position tracking system, the tool comprising:
 a core comprising a ferromagnetic material; and
 an outer coating layer on the core, the coating layer comprising a conductive material configured to produce eddy current distortion responsively to the magnetic field so as to cancel at least part of a distortion caused by the core in a magnetic field generated by the magnetic position tracking system.

26. The tool according to claim 25, wherein the medical tool comprises an orthopedic tool for use with orthopedic implants.

27. The tool according to claim 25, wherein the outer coating layer comprises copper.

28. The tool according to claim 25, wherein the outer coating layer has a pattern of slots formed therein so as to control a formation of the eddy current distortion caused by the coating layer.

29. The tool according to claim 25, wherein the tool further comprises an electrically conducting loop-shaped element having an electrical discontinuity introduced therein so as to reduce eddy current distortion caused by the loop-shaped element in the magnetic field generated by the magnetic position system.

30. A method for treatment of a body of a patient, comprising:
 generating a magnetic field using a first field transducer;
 sensing the magnetic field using a second field transducer, wherein one of the field transducers is coupled to an implant in the body, so as to determine a position of the implant; and
 treating the body using a medical tool, which comprises a first plurality of layers comprising an electrically conductive material, interleaved with a second plurality of layers comprising an electrically insulating material, wherein the layers are arranged to reduce eddy current distortion in the magnetic field sensed by the second field transducer coupled to the implant.

31. The method according to claim 30, wherein the layers in the first and second pluralities respectively comprise first and second planar layers.

32. The method according to claim 30, wherein the tool has an axis, and wherein the layers in the first and second pluralities respectively comprise first and second annular layers surrounding the axis.

33. The method according to claim 30, wherein at least one of the layers in the first plurality has an electrical discontinuity introduced therein so as to reduce the eddy current distortion.

34. The method according to claim 30, wherein treating the body comprises performing an orthopedic procedure using the tool.

35. The method according to claim 30, wherein the second plurality of layers comprises at least one of an adhesive material applied between the first plurality of layers, and an electrically insulating coating layer applied to the first plurality of layers.

36. The method according to claim 30, wherein the tool further comprises a core comprising a ferromagnetic material and an outer coating layer on the core, the coating layer comprising a conductive material configured to produce eddy current distortion responsively to the magnetic field so as to cancel at least some of a distortion caused by the core in the magnetic field sensed by the second field transducer.

37. The method according to claim 30, wherein the tool further comprises an electrically conducting loop-shaped element having an electrical discontinuity introduced therein so as to reduce eddy current distortion caused by the loop-shaped element in the magnetic field sensed by the second field transducer.

38. The method according to claim 30, and comprising determining a position of the medical tool using a third field transducer coupled to the medical tool.

39. The method according to claim 30, wherein the first field transducer comprises a field generator external to the body, and wherein the second field transducer comprises a position sensor coupled to the implant.

40. The method according to claim 30, wherein the first field transducer comprises a field generator coupled to the implant, and wherein the second field transducer comprises a position sensor external to the body.

41. A method for treatment of a body of a patient, comprising:
generating a magnetic field using a first field transducer;
sensing the magnetic field using a second field transducer, wherein the second field transducer is coupled to an implant in the body, so as to determine a position of the implant; and
treating the body using a medical tool, which comprises a core comprising a ferromagnetic material and an outer coating layer on the core, the coating layer comprising a conductive material configured to produce eddy current distortion responsively to the magnetic field so as to cancel at least some of a distortion caused by the core in the magnetic field sensed by the second field transducer coupled to the implant.

42. The method according to claim 41, wherein treating the body comprises performing an orthopedic procedure using the tool.

43. The method according to claim 41, wherein the outer coating layer comprises copper.

44. The method according to claim 41, wherein the outer coating layer has a pattern of slots formed therein, so as to control a formation of the eddy current distortion caused by the coating layer.

45. The method according to claim 41, wherein the tool further comprises an electrically conducting loop-shaped element having an electrical discontinuity introduced therein so as to reduce eddy current distortion caused by the loop-shaped element in the magnetic field sensed by the second field transducer.

46. A method for manufacturing a medical tool for operating in a working volume of a magnetic position tracking system, the method comprising:
forming a first plurality of layers comprising an electrically conductive material; and
interleaving the first plurality with a second plurality of layers comprising an electrically insulating material, wherein the layers are arranged to reduce eddy current distortion in a magnetic field generated by the magnetic position tracking system.

47. The method according to claim 46, wherein the layers in the first and second pluralities respectively comprise first and second planar layers.

48. The method according to claim 46, wherein the tool has an axis, and wherein the layers in the first and second pluralities respectively comprise first and second annular layers surrounding the axis.

49. The method according to claim 46, wherein forming the first plurality of layers comprises introducing an electrical discontinuity into at least one of the layers in the first plurality so as to reduce the eddy current distortion.

50. A method for manufacturing a medical tool for operating in a working volume of a magnetic position tracking system, the method comprising:
forming a core of the tool, the core comprising a ferromagnetic material; and
coating the core with an outer coating layer, the coating layer comprising a conductive material configured to produce eddy current distortion so as to cancel at least part of a distortion caused by the core when subjecting the tool to a magnetic field in the working volume.

51. The method according to claim 50, wherein coating the core comprises applying a pattern of slots in the outer coating layer, so as to control a formation of the eddy current distortion caused by the coating layer.

* * * * *